US 8,481,972 B2

(12) United States Patent
Watanabe

(10) Patent No.: US 8,481,972 B2
(45) Date of Patent: Jul. 9, 2013

(54) FLUOROSCOPY APPARATUS AND FLUOROSCOPY METHOD

(75) Inventor: Toshiaki Watanabe, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/608,541

(22) Filed: Sep. 10, 2012

(65) Prior Publication Data

US 2013/0003922 A1    Jan. 3, 2013

Related U.S. Application Data

(63) Continuation of application No. PCT/JP2011/056017, filed on Mar. 15, 2011.

(30) Foreign Application Priority Data

Mar. 18, 2010   (JP) .................................. 2010-062548

(51) Int. Cl.
*G01N 21/64* (2006.01)

(52) U.S. Cl.
USPC ...................................................... 250/458.1

(58) Field of Classification Search
USPC ...................................................... 250/458.1
See application file for complete search history.

(56) References Cited

U.S. PATENT DOCUMENTS

| 2001/0056238 | A1* | 12/2001 | Tsujita | 600/476 |
|---|---|---|---|---|
| 2003/0218137 | A1* | 11/2003 | Sendai | 250/461.1 |
| 2006/0025692 | A1 | 2/2006 | Ishihara | |
| 2007/0177153 | A1* | 8/2007 | Takahashi | 356/479 |
| 2007/0197874 | A1 | 8/2007 | Ishihara | |
| 2009/0036743 | A1 | 2/2009 | Yabe et al. | |
| 2010/0020163 | A1 | 1/2010 | Watanabe et al. | |
| 2010/0103250 | A1 | 4/2010 | Ishihara | |

FOREIGN PATENT DOCUMENTS

| JP | 62-247232 | 10/1987 |
|---|---|---|
| JP | 3-58729 | 9/1991 |
| JP | 2001-169999 | 6/2001 |
| JP | 2003-528 | 1/2003 |
| JP | 2006-61683 | 3/2006 |
| JP | 2006-175052 | 7/2006 |
| JP | 2007-222381 | 9/2007 |
| JP | 2008-183349 | 8/2008 |
| JP | 2009-34224 | 2/2009 |
| JP | 2009-279172 | 12/2009 |
| WO | WO 2008/072579 A1 | 6/2008 |

OTHER PUBLICATIONS

International Search Report dated Apr. 19, 2011 issued in PCT/JP2011/056017.

* cited by examiner

*Primary Examiner* — Constantine Hannaher
(74) *Attorney, Agent, or Firm* — Scully, Scott, Murphy & Presser, P.C.

(57) ABSTRACT

A fluoroscopy apparatus that includes an illumination section including a light source for radiating illumination light and excitation light onto a subject; a fluoroscopic image acquisition section acquiring a fluoroscopic image of fluorescence generated in the subject; a return-light image acquisition section acquiring a reference image of return light returning from the subject; a distance-information acquisition section acquiring information about a distance between the return-light image acquisition section and the subject; and an image correction section correcting the fluoroscopic image by using the reference image. The image correction section sets a correction coefficient based on the distance information, generates a correction reference image or a correction fluoroscopic image by performing a power calculation for light intensity information of the reference image and/or the fluoroscopic image by using the correction coefficient as an index, and divides the correction fluoroscopic image by the correction reference image.

10 Claims, 14 Drawing Sheets

FIG. 8

| BOUNDARY VALUE | NORMALIZED FLUORESCENCE SIGNAL INTENSITY | | | | NORMALIZED REFERENCE SIGNAL INTENSITY | | | |
|---|---|---|---|---|---|---|---|---|
| | BOUNDARY VALUE OR LESS | | BOUNDARY VALUE OR MORE | | BOUNDARY VALUE OR LESS | | BOUNDARY VALUE OR MORE | |
| | INDEX $\alpha_1$ | DETERMINED COEFFICIENT $R^2$ | INDEX $\alpha_2$ | DETERMINED COEFFICIENT $R^2$ | INDEX $\beta_1$ | DETERMINED COEFFICIENT $R^2$ | INDEX $\beta_2$ | DETERMINED COEFFICIENT $R^2$ |
| D(3) | -0.577 | 0.9786 | -1.37 | 0.9853 | -0.868 | 0.9804 | -1.69 | 0.9972 |
| D(4) | -0.639 | 0.9778 | -1.45 | 0.9951 | -0.979 | 0.9746 | -1.73 | 0.9986 |
| ... | ... | ... | ... | ... | ... | ... | ... | ... |
| D(5) | -0.94 | 0.9672 | -1.66 | 0.9981 | -1.30 | 0.9721 | -1.84 | 0.9998 |

FLUOROSCOPY APPARATUS AND FLUOROSCOPY METHOD

CROSS-REFERENCE TO RELATED APPLICATIONS

This is a continuation of International Application PCT/JP2011/056017, with an international filing date of Mar. 15, 2011, which is hereby incorporated by reference herein in its entirety. This application claims the benefit of Japanese Patent Application No. 2010-062548, the contents of which are incorporated herein by reference.

TECHNICAL FIELD

The present invention relates to a fluoroscopy apparatus and a fluoroscopy method.

BACKGROUND ART

There are conventionally-known methods for correcting a fluctuation in brightness of a fluoroscopic image due to observation distance, by dividing the fluoroscopic image by a reflected-light image (for example, see PTLs 1 to 3).

CITATION LIST

Patent Literature

{PTL 1} Japanese Unexamined Patent Application, Publication No. Sho 62-247232
{PTL 2} Japanese Examined Patent Application, Publication No Hei 3-58729
{PTL 3} Japanese Unexamined Patent Application, Publication No. 2006-175052

SUMMARY OF INVENTION

According to a first aspect, the present invention provides a fluoroscopy apparatus including: an illumination section that includes a light source for radiating illumination light and excitation light onto a subject; a fluoroscopic image acquisition section that acquires a fluoroscopic image of fluorescence generated in the subject irradiated with the excitation light from the illumination section; a return-light image acquisition section that acquires a reference image of return light returning from the subject irradiated with the illumination light from the illumination section; a distance-information acquisition section that acquires information about a distance between the return-light image acquisition section and the subject; and an image correction section that corrects the fluoroscopic image acquired by the fluoroscopic image acquisition section, by using the reference image acquired by the return-light image acquisition section, in which the image correction section sets a correction coefficient based on the distance information acquired by the distance-information acquisition section, generates a correction reference image or a correction fluoroscopic image by performing a power calculation for light intensity information of at least one of the reference image and the fluoroscopic image by using the set correction coefficient as an index, and divides the correction fluoroscopic image by the generated correction reference image.

According to the first aspect of the present invention, when the excitation light is radiated from the illumination section onto the subject, a fluorescent material existing in the subject is excited to generate fluorescence. The generated fluorescence is captured by the fluoroscopic image acquisition section, thereby acquiring a fluoroscopic image. On the other hand, when the illumination light is radiated from the illumination section onto the subject, return light returning by being reflected on the surface of the subject is captured by the return-light image acquisition section, thereby acquiring a reference image. The acquired fluoroscopic image is corrected in the image correction section by using the reference image.

Here, the intensity signal at each pixel of the acquired fluoroscopic image and the intensity signal at each pixel of the reference image have different dependencies on distance. Therefore, the dependence can be reduced by applying a power calculation with a certain index to the intensity signals of the reference image and the fluoroscopic image. In this case, because reflected light of illumination light constituting the reference image and fluorescence constituting the fluoroscopic image travel in different routes, the dependence on the distance also fluctuates depending on the distance.

In the above-described invention, the distance-information acquisition section may acquire the distance information from a signal intensity of the reference image acquired by the return-light image acquisition section.

The above-described invention may further include a distance control section that moves the subject toward or away from the return-light image acquisition section, in which the distance-information acquisition section may be a displacement sensor provided in the distance control section.

In the above-described invention, the image correction section may include a correction coefficient storage that stores the distance information in association with the correction coefficient; and the correction coefficient stored in the correction coefficient storage may be read by using the distance information acquired by the distance-information acquisition section.

According to a second aspect, the present invention provides a fluoroscopy method including: radiating, from an illumination section, illumination light and excitation light onto a subject; acquiring a fluoroscopic image of fluorescence generated in the subject irradiated with the excitation light from the illumination section; acquiring, with a return-light image acquisition section, a reference image of return light returning from the subject irradiated with the illumination light from the illumination section; acquiring information about a distance between the return-light image acquisition section and the subject; and setting a correction coefficient based on the acquired distance information, generating a correction fluoroscopic image or a correction reference image by performing a power calculation for light intensity information of at least one of the reference image and the fluoroscopic image by using the set correction coefficient as an index, and dividing the correction fluoroscopic image by the generated correction reference image.

BRIEF DESCRIPTION OF DRAWINGS

FIG. 1 is a diagram showing the entire configuration of a fluoroscopy apparatus according to one embodiment of the present invention.

FIG. 2 is a block diagram showing an inner configuration of an image correction section of the fluoroscopy apparatus shown in FIG. 1.

FIG. 3 is a diagram for explaining a process of setting correction coefficients and a boundary value in the fluoroscopy apparatus shown in FIG. 1.

FIG. 4 is a flowchart showing the process of FIG. 3.

FIG. 8 is a diagram showing a database obtained after a power approximation is performed in FIG. 7.

DESCRIPTION OF EMBODIMENTS

A fluoroscopy apparatus 1 and a fluoroscopy method according to one embodiment of the present invention will be described below with reference to the drawings.

Figure 1:
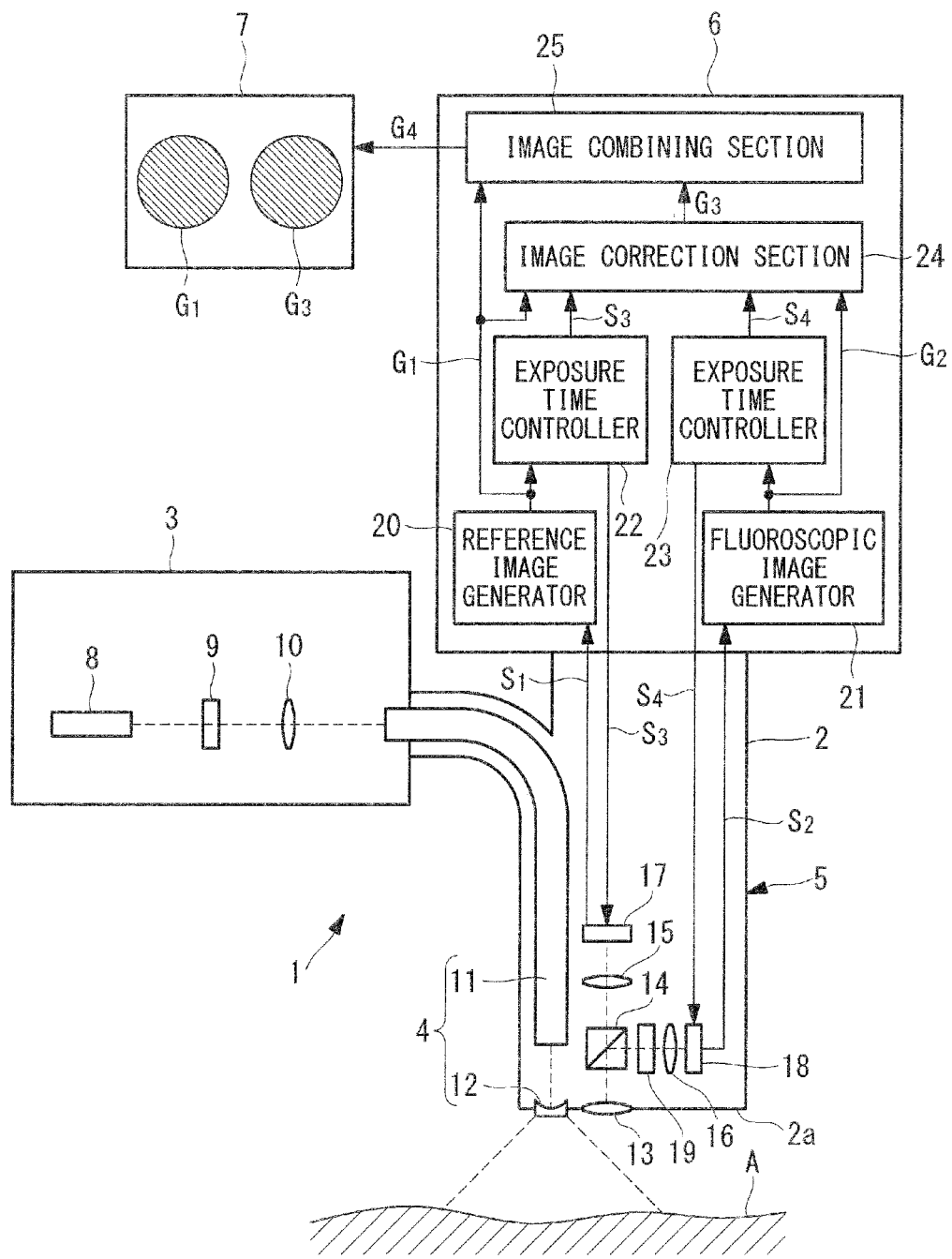

The fluoroscopy apparatus 1 of this embodiment is an endoscopic apparatus and includes, as shown in FIG. 1, an elongated insert member 2 to be inserted into the body; a light source (illumination section) 3; an illumination unit (illumination section) 4 that radiates illumination light and excitation light emitted from the light source 3, from the tip of the insert member 2 toward an observation target A; an image acquisition unit 5 that is provided at the tip of the insert member 2 and acquires image information of body tissue serving as the observation target A; an image processing section 6 that is disposed at a base end of the insert member 2 and processes the image information acquired by the image acquisition unit 5; and a monitor 7 that displays an image $G_4$ processed by the image processing section 6.

The light source 3 includes a xenon lamp 8; a filter 9 that extracts excitation light and illumination light (for example, a wavelength band from 400 to 750 nm) from the illumination light emitted from the xenon lamp 8; and a coupling lens 10 that focuses the excitation light and the illumination light extracted by the filter 9.

The illumination unit 4 includes a light guide fiber 11 that is longitudinally disposed along almost the entire length of the insert member 2 and guides the excitation light and the illumination light focused by the coupling lens 10; and an illumination optical system 12 that is provided at the tip of the insert member 2 and spreads out the excitation light and the illumination light guided by the light guide fiber 11 to radiate them onto the observation target A facing a tip surface $2a$ of the insert member 2.

The image acquisition unit 5 includes an objective lens 13 that collects return light returning from a predetermined observation region of the observation target A; a dichroic mirror (branching portion) 14 that reflects light having a wavelength equal to or longer than an excitation wavelength (excitation light and fluorescence) and transmits illumination light having a wavelength shorter than the excitation wavelength, among the return light collected by the objective lens 13; two focusing lens (image-acquisition optical systems) 15 and 16 that focus the illumination light transmitted through the dichroic mirror 14 and the fluorescence reflected by the dichroic mirror 14, respectively; and two image acquisition devices 17 and 18, such as CCDs, that acquire images of the illumination light and the fluorescence focused by the focusing lenses 15 and 16. In the figure, reference numeral 19 denotes an excitation-light cut filter that cuts out excitation light from the light reflected by the dichroic mirror 14 (for example, transmits only light having a wavelength band from 765 to 850 nm).

The image processing section 6 includes a reference image generator (RI generator) 20 that generates a reference image $G_1$ from reference image information $S_1$ acquired by the image acquisition device 17; a fluoroscopic image generator (FI generator) 21 that generates a fluoroscopic image $G_2$ from fluoroscopic image information $S_2$ acquired by the image acquisition device 18; exposure time controllers (ET controllers) 22 and 23 that calculate exposure times $S_3$ and $S_4$ of the image acquisition devices 17 and 18 based on the reference image $G_1$ and the fluoroscopic image $G_2$, generated by the reference image generator 20 and the fluoroscopic image generator 21, respectively, to control the exposures of the image acquisition devices 17 and 18; an image correction section 24 that receives the reference image $G_1$, the fluoroscopic image $G_2$, and the exposure times $S_3$ and $S_4$ of the image acquisition devices 17 and 18 and that corrects the fluoroscopic image $G_2$ by using the reference image $G_1$; and an image combining section 25 that generates an image $G_4$ by combining the reference image $G_1$ and a corrected fluoroscopic image $G_3$ obtained after the correction performed by the image correction section 24.

Figure 2:
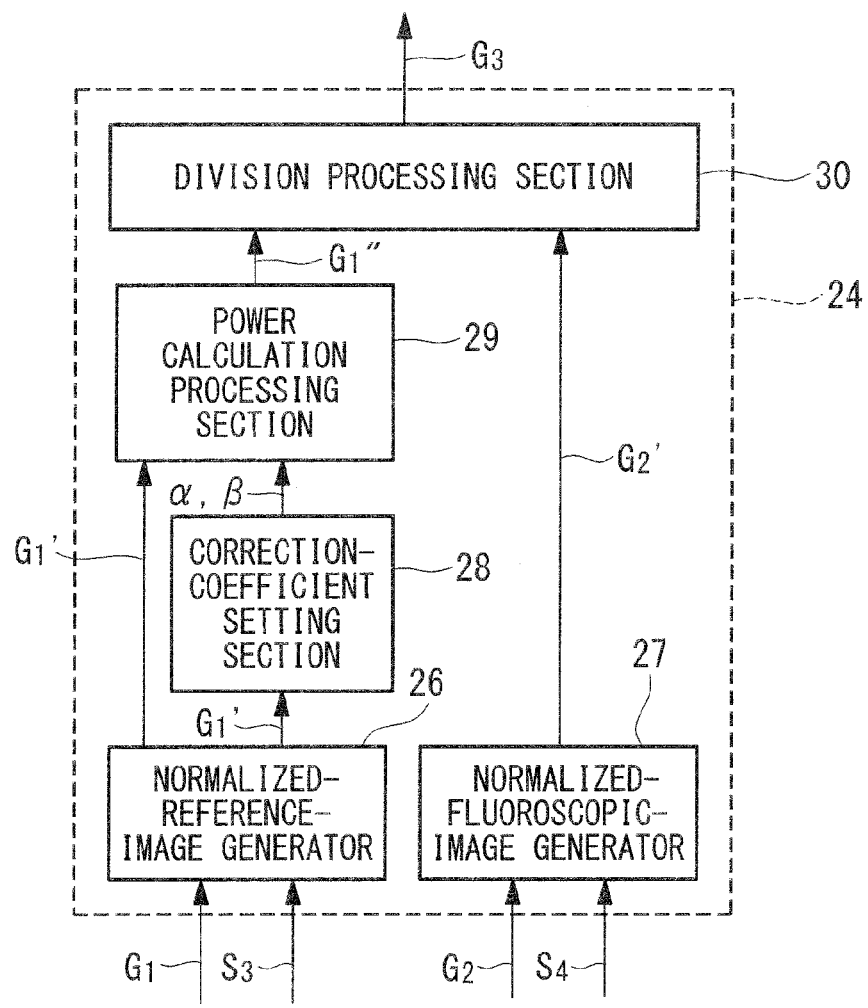

As shown in FIG. 2, the image correction section 24 includes a normalized-reference-image generator (distance-information acquisition section) 26 and a normalized-fluoroscopic-image generator 27 that generate a normalized reference image $G_1'$ and a normalized fluoroscopic image $G_2'$ from the reference image $G_1$ and the fluoroscopic image $G_2$, respectively; a correction-coefficient setting section 28 that sets correction coefficients $\alpha$ and $\beta$ based on the normalized reference image $G_1'$ generated by the normalized-reference-image generator 26; a power calculation processing section 29 that performs a power calculation for the normalized reference image $G_1'$ by using the correction coefficients $\alpha$ and $\beta$ set by the correction-coefficient setting section 28 as indices; and a division processing section 30 that divides a correction reference image $G_1''$, obtained after the power calculation performed by the power calculation processing section 29, by the normalized fluoroscopic image $G_2'$.

The normalized-reference-image generator 26 and the normalized-fluoroscopic-image generator 27 divide the reference image $G_1$ and the fluoroscopic image $G_2$ by the exposure times $S_3$ and $S_4$ of the image acquisition devices 17 and 18, which are controlled by the exposure time controllers 22 and 23, respectively, thereby generating the normalized reference image $G_1$ and the normalized fluoroscopic image $G_2'$. Thus, fluctuations in the overall signal intensities of the reference image $G_1$ and the fluoroscopic image $G_2$, which depend on the exposure times $S_3$ and $S_4$ of the image acquisition devices 17 and 18, are eliminated to obtain the normalized reference image $G_1'$ and the normalized fluoroscopic image $G_2'$.

The correction-coefficient setting section 28 stores the indices $\alpha$ and $\beta$, serving as the correction coefficients, in association with, for example, distance information from the tip surface $2a$ of the insert member 2 to the surface of the observation target A (hereinafter, referred to as observation distance information), Specifically, since the signal intensity at each pixel of the normalized reference image $G_1'$ is associated with an observation distance D on a one-to-one basis, the indices $\alpha$ and $\beta$ are stored in association with the signal intensity. By doing so, it is possible to acquire the observation distance information without using a special sensor and to acquire a highly-quantitative fluoroscopic image $G_2$.

In this embodiment, a predetermined boundary value D(n) of the signal intensity is set, and two different correction coefficients $\alpha_1$ and $\alpha_2$ and two different correction coefficients $\beta_1$ and $\beta_2$ are stored before and after the boundary value D(n). Then, the correction-coefficient setting section 28 compares the signal intensity at each pixel of the normalized reference image $G_1'$, sent from the normalized-reference-image generator 26, with the boundary value D(n), sets first correction coefficients $\alpha_1$ and $\beta_1$ when the signal intensity at each pixel of the normalized reference image $G_1'$ is less than the boundary value D(n), and sets second correction coefficients $\alpha_2$ and $\beta_2$ when the signal intensity at each pixel of the normalized reference image $G_1'$ is equal to or greater than the boundary value D(n).

In this case, two correction coefficients $\alpha$ and $\beta$ and the boundary value D(n) are determined as described below, through measurement prior to fluoroscopy.

Figure 3:
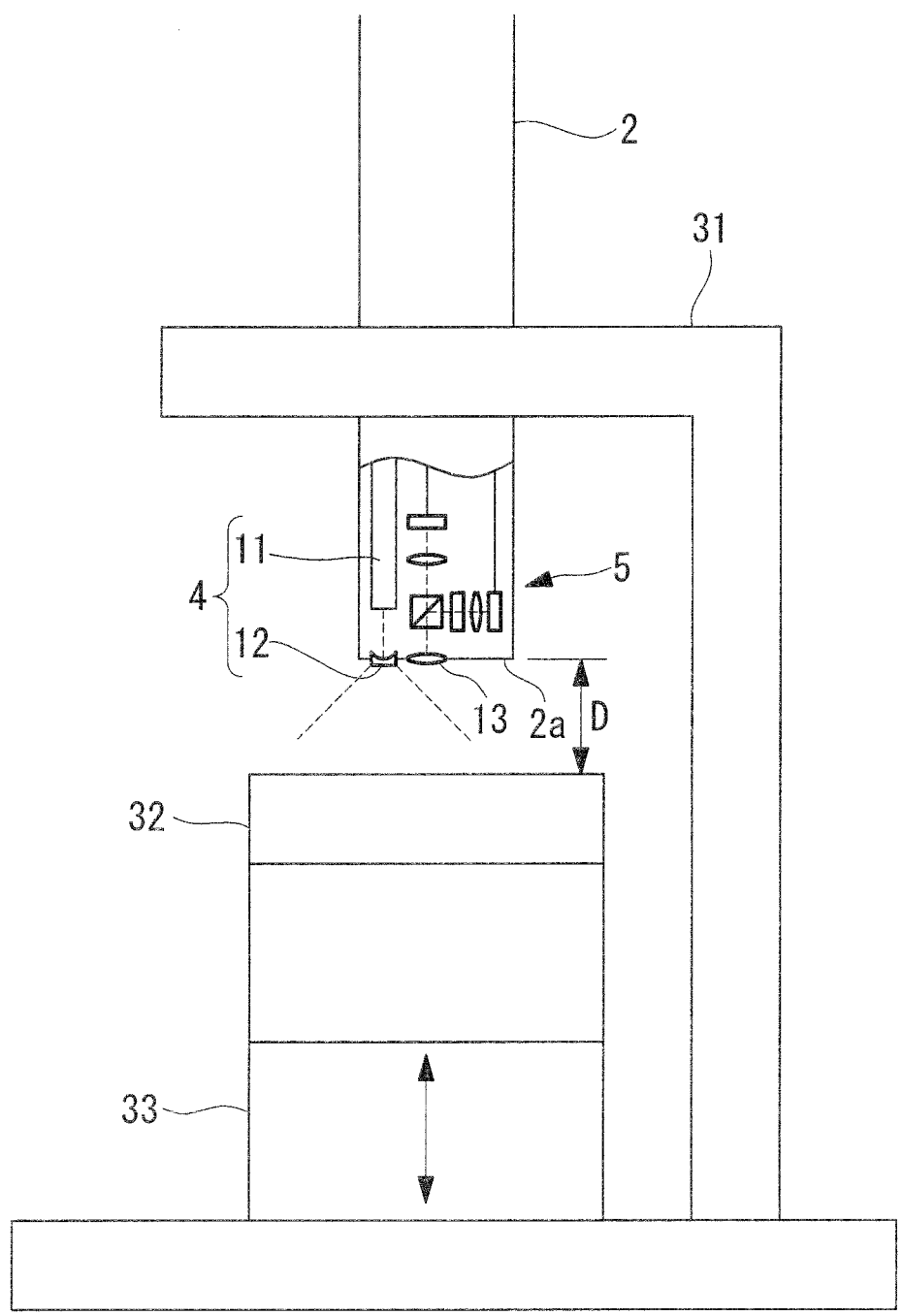

Specifically, to determine the correction coefficients $\alpha$ and $\beta$ and the boundary value D(n), as shown in FIG. 3, a holder 31 that secures the insert member 2, a standard specimen 32 that is placed facing the tip surface 2a of the insert member 2 secured by the holder 31 with the observation distance D therebetween, and a vertical motion stage 33 that changes the observation distance D between the tip surface 2a of the insert member 2 and the standard specimen 32 are prepared. A displacement sensor (not shown), such as an encoder, is provided in the vertical motion stage 33. By doing so, it is possible to directly acquire the observation distance information with the displacement sensor and to acquire a highly-quantitative fluoroscopic image $G_2$.

As the standard specimen 32, a phantom having scattering and absorbing characteristics similar to those of the living body to be observed may be used, or excised tissue from a human or an animal (pig, mouse, or the like) may be used.

Figure 4:
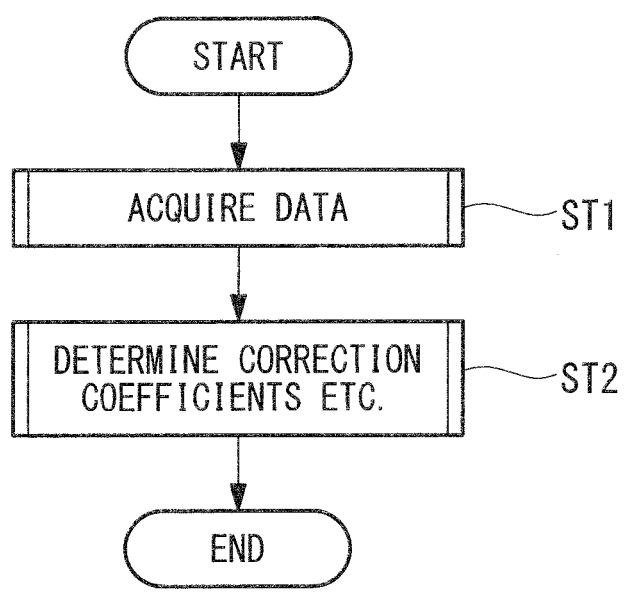
Figure 5:
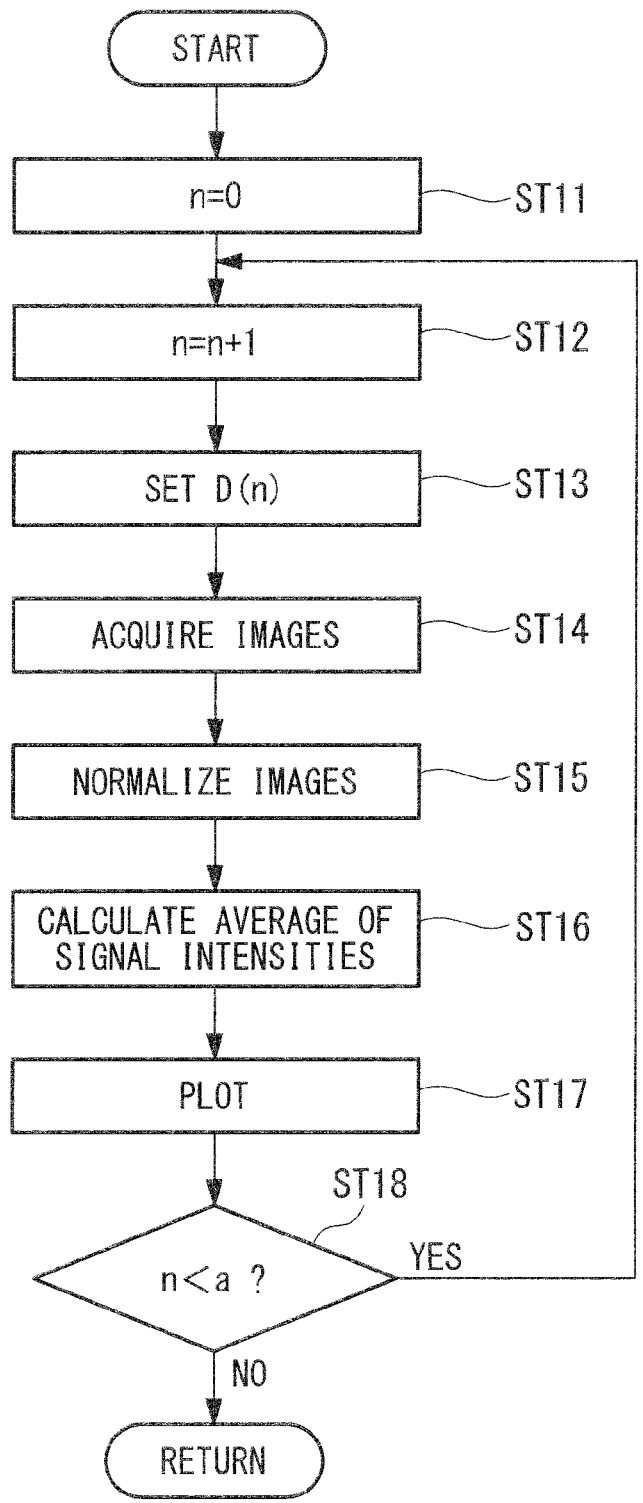
FIG. 5 is a flowchart showing a data acquisition step in the process of FIG. 4.
Figure 6:
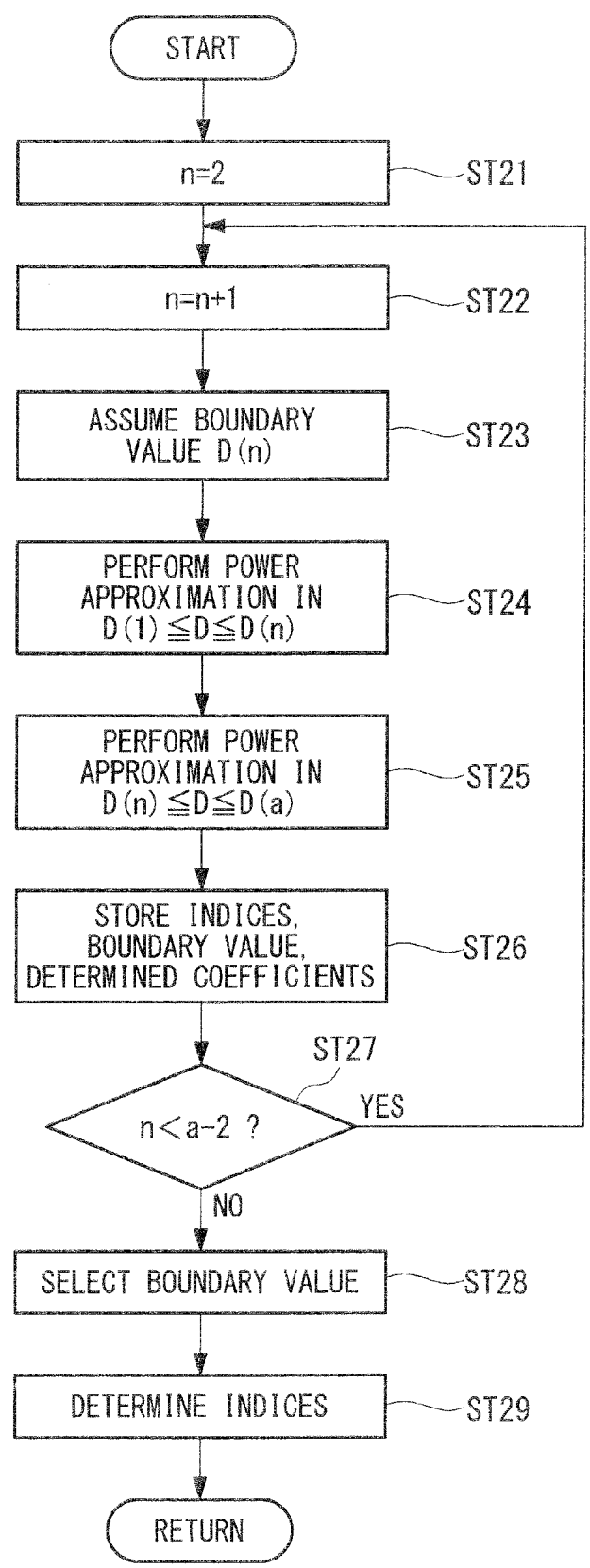
FIG. 6 is a flowchart showing a correction-coefficient determination step in the process of FIG. 4.

According to flowcharts shown in FIGS. 4 to 6, a data acquisition step ST1 and a correction-coefficient determination step ST2 are performed.

Figure 7:
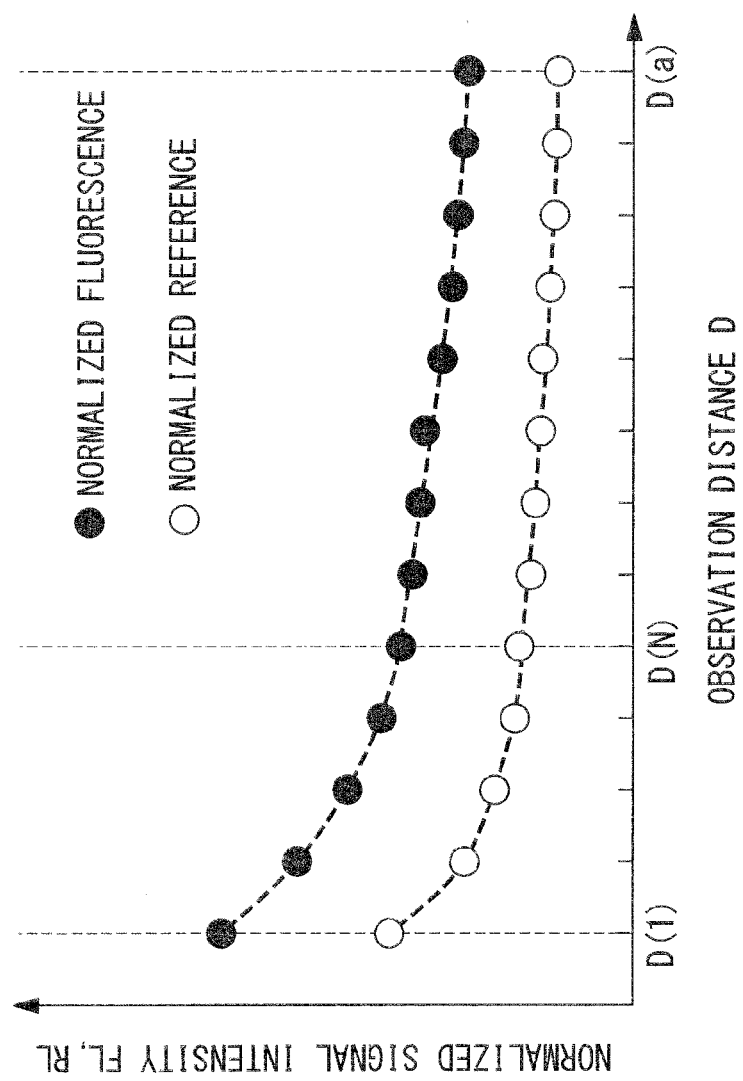
FIG. 7 is a plot showing the relationship between observation distance and signal intensity obtained through the process of FIG. 4.

First, in the data acquisition step ST1, as shown in FIG. 5, n is initialized (ST11 and ST12). The vertical motion stage 33 is operated to precisely set observation distance D(n) (n is a natural number) with the displacement sensor (ST13). The reference image $G_1$ and the fluoroscopic image $G_2$ are acquired at this time (ST14). The normalized reference image $G_1'$ and the normalized fluoroscopic image $G_2'$ are calculated (ST15). The average signal intensity in a preset region of interest is calculated (ST16). The average is plotted as the value of the signal intensity with respect to the observation distance D(n) (ST17). This process is repeated (ST18) to obtain a plurality of (a) points, as shown in FIG. 7.

The size of the region of interest may be fixed irrespective of the observation distance D if the fluorescence intensity in the standard specimen 32 is uniform. If the standard specimen 32 has an uneven surface or if the distribution of fluorescence in the standard specimen 32 is non-uniform, it is preferable that the size of the region of interest be reduced as the observation distance D is increased, to always obtain the signal intensity in the same region.

Next, in the correction-coefficient determination step ST2, as shown in FIG. 6, first, n is set to 3 (ST21 and ST22). The observation distance D(n) at an n-th point is set as a boundary value (ST23). The reason why D(3) is set as the first boundary value is because data of three or more points is required in order to use a power approximation, such as the least squares method.

Then, a power approximation is performed in a zone from observation distance D(1) to D(n) and in a zone from D(n) to D(a) (ST24 and ST25) to calculate indices. Determined coefficients $R^2$ and the boundary value D(n) are stored in association with each other (ST26).

Then, n is incremented by one (ST22), and the above-described process is repeated until n becomes a-2 (ST27) to obtain a data table shown in FIG. 8. From the data table, a combination of the boundary value D(n) and the indices $\alpha$ and $\beta$ at which the sum of the determined coefficients $R^2$ is closest to 4 is selected (ST28) and is stored in the correction-coefficient setting section 28 (ST29).

In this embodiment, the index a obtained for the fluoroscopic image $G_2$ is divided by the index $\beta$ obtained for the reference image, and an index $\alpha/\beta$ is stored as a correction coefficient.

The power calculation processing section 29 applies power calculation processing to the intensity signal (light intensity information) at each pixel of the normalized reference image $G_1'$ by using, as the index, the correction coefficient $\alpha/\beta$ set in the correction-coefficient setting section 28, thus generating the correction reference image $G_1''$. The correction reference image $G_1''$ generated in the power calculation processing section 29 is input to the division processing section 30. On the other hand, as for the fluoroscopic image, the normalized fluoroscopic image $G_2'$ is input to the division processing section 30 as a correction fluoroscopic image, without any change.

In this specification, when the normalized fluoroscopic image is input to the division processing section 30 as a correction fluoroscopic image without being subjected to power calculation processing, i.e., without any change, the input normalized fluoroscopic image is called the correction fluoroscopic image. Similarly, when the normalized reference image is input to the division processing section 30 as a correction reference image without being subjected to power calculation processing, i.e., without any change, the input normalized reference image is called the correction reference image.

The division processing section 30 divides the correction fluoroscopic image $G_2'$ by the correction reference image $G_1''$, for each pixel, thereby generating the corrected fluoroscopic image $G_3$.

The image combining section 25 combines the image $G_4$ such that the reference image $G_1$ and the corrected fluoroscopic image $G_3$ are arranged in parallel so as to be simultaneously displayed on the monitor 7, for example, and outputs the image $G_4$ to the monitor 7.

A description will be given below of the result of confirmation of the effect of correction and calculation of the correction coefficients, through the process shown in FIG. 3 for setting the correction coefficients and the boundary value, in the fluoroscopy apparatus shown in FIG. 1.

Note that a mixture of fluorescence agent solution and a scattering material is used as a standard specimen to be observed.

Figure 13:
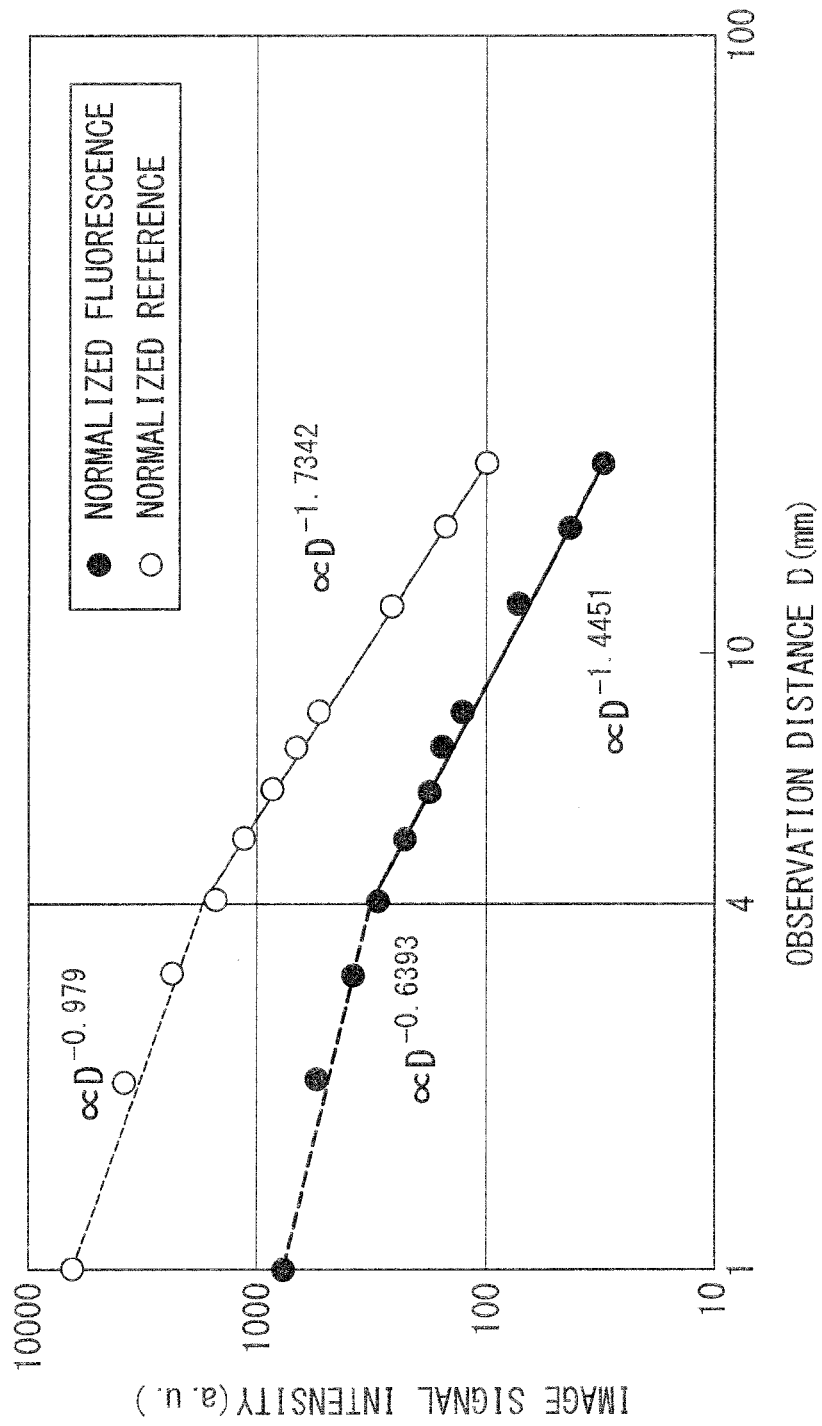
FIG. 13 is a plot showing the relationship between observation distance and signal intensity obtained after the flow of FIG. 6 is performed in the fluoroscopy apparatus shown in FIG. 1.

FIG. 13 is a plot showing the relationship between the observation distance and the signal intensity, which is obtained after the flow of FIG. 6 is performed in the fluoroscopy apparatus shown in FIG. 1. The vertical axis indicates the signal intensity of the normalized reference image and the signal intensity of the normalized fluoroscopic image on a logarithmic scale, and the horizontal axis indicates the observation distance on a logarithmic scale. As a result of the flow of FIG. 6, 4 mm is selected as the boundary value P in ST28, as shown in FIG. 13. Note that expressions described in FIG. 13 are approximate values obtained when a power approximation is performed in ST24 and ST25.

Figure 14:
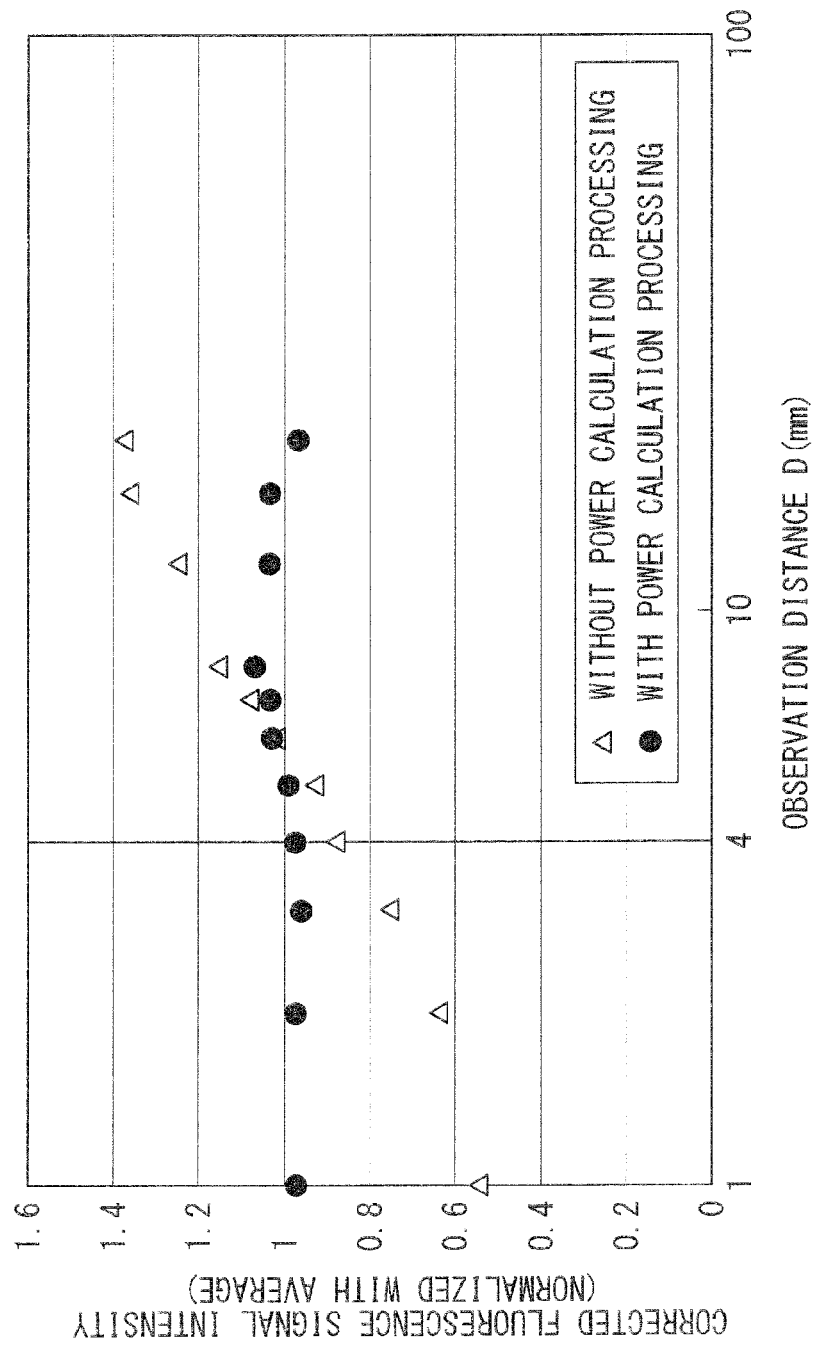
FIG. 14 is a plot showing the result of an effect of power calculation processing, by using the results from studying FIG. 13.

FIG. 14 is a plot showing the result of the effect of power calculation processing, by using the results from studying FIG. 13. The case "without power calculation processing" shows results obtained by dividing the fluoroscopic image by the reference image, as in a conventional example. The case "with power calculation processing" shows results obtained after power calculation processing is performed in the image correction section by using the indices obtained through the flow of FIG. 6.

In each of the cases, corrected fluoroscopic images are generated at respective observation distances. The average signal intensities in an ROI (region of interest) in the vicinity of the center of the generated corrected fluoroscopic images are calculated, are normalized by their average in respective conditions (11 points with different distances), and are plotted. This shows that errors are reduced after power calculation processing is applied.

A fluoroscopy method using the thus-configured fluoroscopy apparatus 1 of this embodiment will be described below.

According to the fluoroscopy apparatus 1 of this embodiment, illumination light and excitation light emitted from the light source 3 are radiated via the illumination unit 4 from the tip surface 2a of the insert member 2 onto the observation target (subject) A, light reflected on the surface of the observation target A is acquired by the image acquisition device 17, and the reference image $G_1$ is generated by the reference image generator 20. On the other hand, fluorescence generated in the observation target A irradiated with the excitation light is acquired by the image acquisition device 18, and the fluoroscopic image $G_2$ is generated by the fluoroscopic image generator 21.

When the reference image $G_1$ and the fluoroscopic image $G_2$ are generated, the exposure time controllers 22 and 23 calculate the exposure times $S_3$ and $S_4$ of the image acquisition devices 17 and 18 based on the generated reference image $G_1$ and fluoroscopic image $G_2$, to automatically control exposures of the image acquisition devices 17 and 18. The reference image $G_1$, the fluoroscopic image $G_2$, and the exposure times $S_3$ and $S_4$ of the image acquisition devices 17 and 18 obtained when these images are acquired are sent to the image correction section 24.

In the image correction section 24, the normalized-reference-image generator 26 divides the reference image $G_1$ by the exposure time $S_3$ of the image acquisition device 17 to generate the normalized reference image $G_1'$, and the normalized-fluoroscopic-image generator 27 divides the fluoroscopic image $G_2$ by the exposure time $S_4$ of the image acquisition device 18 to generate the normalized fluoroscopic image $G_2'$.

Then, the correction-coefficient setting section 28 sets the correction coefficients α and β based on the signal intensity at each pixel of the normalized reference image $G_1'$, and the power calculation processing section 29 performs a power calculation for the signal intensity at each pixel by using the correction coefficient α/β set for each pixel, as an index, to generate the correction reference image $G_1''$.

Then, the correction reference image $G_1''$ and the normalized fluoroscopic image $G_2'$, serving as a correction fluoroscopic image, output from the normalized-fluoroscopic-image generator 27, are input to the division processing section 30. The correction fluoroscopic image $G_2$ is divided by the correction reference image $G_1''$, thus generating the corrected fluoroscopic image $G_3$.

The generated corrected fluoroscopic image $G_3$ and the reference image $G_1$ are combined in the image combining section 25 and are displayed in parallel on the monitor 7.

In this way, according to the fluoroscopy apparatus 1 and the fluoroscopy method of the this embodiment, the correction fluoroscopic image $G_2$ is divided by using the correction reference image $G_1''$, which is obtained through a power calculation performed by using, as indices, the correction coefficients $α_1$, $β_1$, $α_2$, and $β_2$ which are different before and after a predetermined observation distance D used as the boundary value D(n). Therefore, an advantage is afforded in that a highly-quantitative corrected fluoroscopic image $G_3$ can be acquired even if the observation distance D fluctuates greatly.

Figure 9:
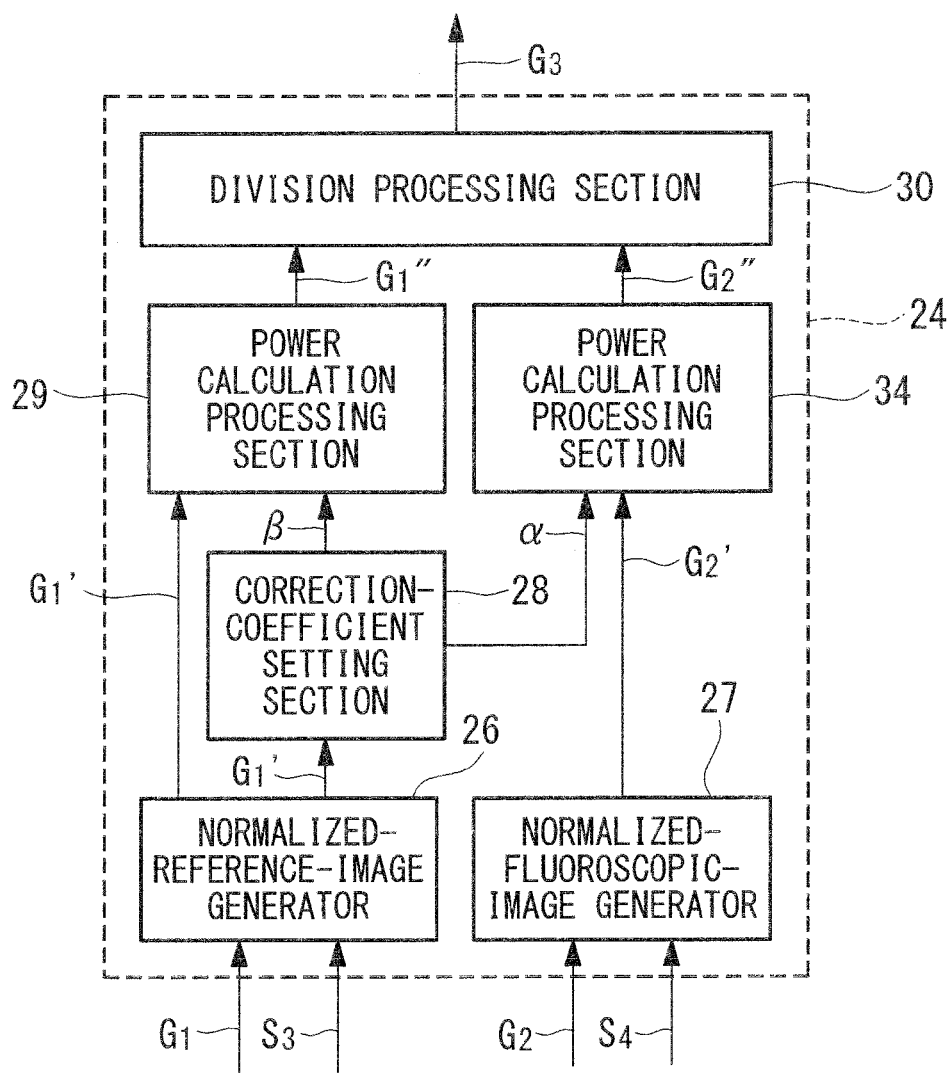
FIG. 9 is a block diagram showing a modification of the image correction section shown in FIG. 2.

In this embodiment, the indices α and β, which are calculated for both of the signal intensity of the normalized fluoroscopic image $G_2'$ and the signal intensity of the normalized reference image $G1'$, are used to apply a power calculation only to the signal intensity of the normalized reference image $G1'$. Therefore, an advantage is afforded in that it is possible to reduce the amount of calculation and to perform rapid calculation, compared with a case where a power calculation is applied to both the normalized fluoroscopic image $G_2'$ and the normalized reference image $G_1'$. Alternatively, as shown in FIG. 9, a configuration may be used in which a power calculation processing section 34 is provided for the normalized fluoroscopic image $G_2'$, and the indices α and β set by the correction-coefficient setting section 28 are used to apply a power calculation with 1/β to the normalized reference image $G_1'$ and to apply a power calculation with 1/α to the normalized fluoroscopic image $G_2'$ to obtain a correction fluoroscopic image $G_2''$.

A Power calculation with the index α, obtained for the normalized fluoroscopic image $G_2'$, may be applied to each pixel of the corrected fluoroscopic image $G_3$ obtained in the division processing section 30 by dividing the correction fluoroscopic image $G_2''$ by the correction reference image $G_1''$. Thus, it is possible to compare the signal intensity at each pixel with the amount of fluorescence in the observation target A and, furthermore, to perform quantitative observation.

Alternatively, a correspondence table (conversion table) of the signal intensity of the corrected fluoroscopic image $G_3$ and the fluorescence concentration may be provided, and the fluorescence concentration of a particular region may be displayed on the image.

Figure 10:
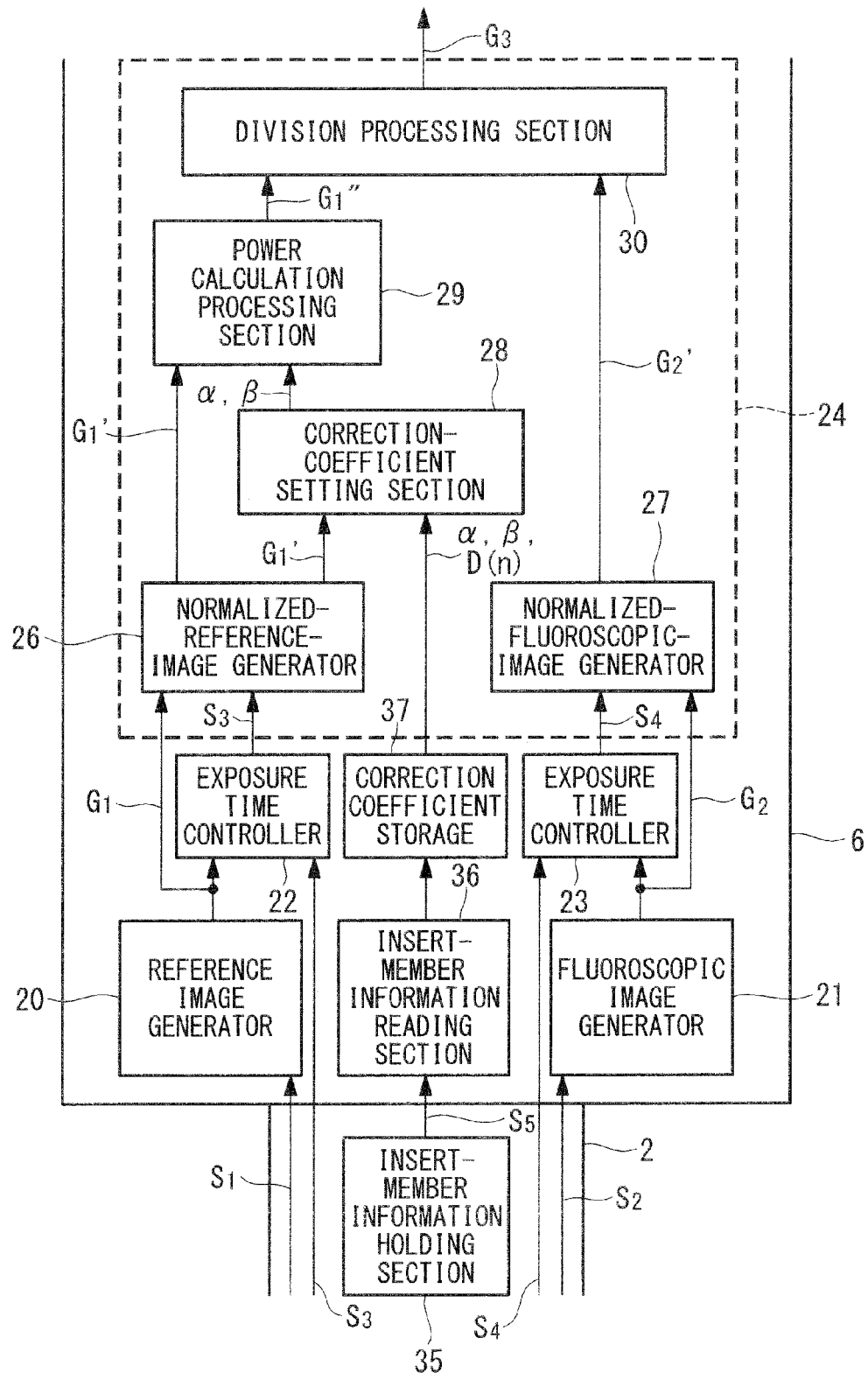
FIG. 10 is a partial block diagram showing a modification of an image processing section provided in the fluoroscopy apparatus shown in FIG. 1.

As shown in FIG. 10, when a detachable insert member 2 is employed, an insert-member information holding section 35 that holds insert-member information $S_5$ may be provided in the insert member 2, and an insert-member information reading section 36 that reads the insert-member information $S_5$ and a correction coefficient storage (CC storage) 37 that stores the correction coefficients α and β and the boundary value D(n) in association with the insert-member information $S_5$ may be provided in the image processing section 6. Thus, when the insert member 2 is attached to the image processing section 6, the insert-member information $S_5$ stored in the insert-member information holding section (IMIH section) 35 of the insert member 2 is read by the insert-member information reading section (IMIR section) 36, and the correction coefficients α and β and the boundary value D(n) stored in the correction coefficient storage 37 in association with the insert-member information are read and stored in the correction-coefficient setting section 28.

By doing so, an advantage is afforded in that fluctuations in correction coefficients due to the individual differences between insert members 2 can be calibrated with accuracy.

Figure 11:
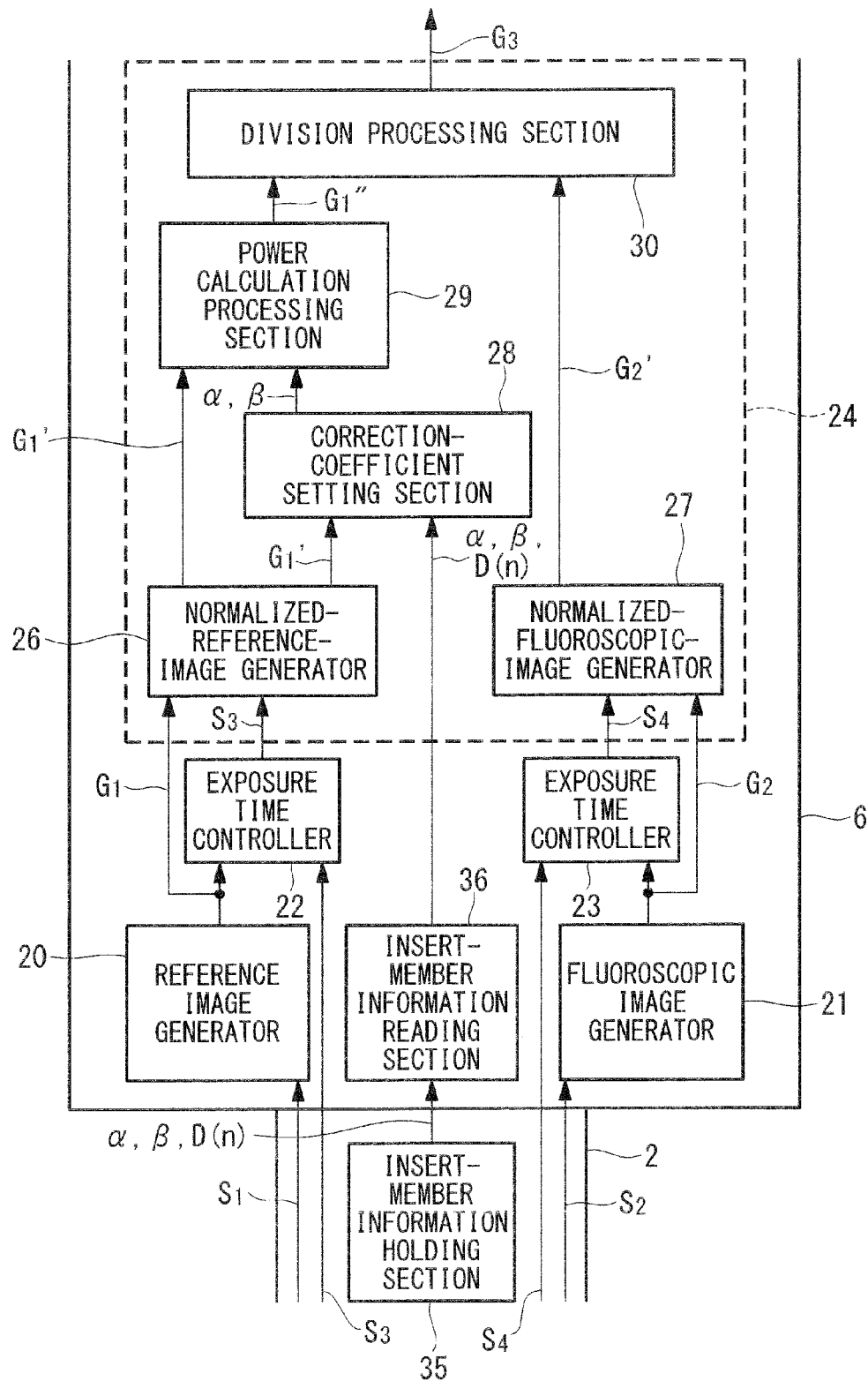
FIG. 11 is a partial block diagram showing another modification of the image processing section provided in the fluoroscopy apparatus shown in FIG. 1.

Furthermore, instead of the configuration in which the insert-member information holding section 35 holds the insert-member information $S_5$ and the correction coefficient storage 37 stores the correction coefficients α and β etc., as shown in FIG. 11, a configuration may be used in which the insert-member information holding section 35 directly stores the correction coefficients α and β and the boundary value D(n), and the correction coefficients α and β and the boundary value D(n) read by the insert-member information reading section 36 are sent to the correction-coefficient setting section 28.

In this embodiment, a single boundary value D(n) is set, and different correction coefficients are set before and after the boundary value D(n); however, instead of this, two or more boundary values D(n) may be set, and three or more correction coefficients may be set. In the case where two or more boundary values D(n) exist, correction coefficients can be set by using the flowcharts shown in FIGS. 4 to 6.

For example, to set three or more correction coefficients, two boundary values D1 and D2 are selected in the observation distance range $D(3) \leq D \leq D(a-2)$, and a power approximation is performed in zones $D(1) \leq D \leq D1$, $D1 \leq D \leq D2$, and $D2 \leq D \leq D(a-2)$, and indices, boundary values, and determined coefficients are stored for each combination of boundary values D1 and D2. From a thus-obtained database, the indices and the boundary values D1 and D2 in which the sum of the determined coefficients is closest to 6 are employed.

To divide the range of the observation distance D by more boundary values, for example, a power approximation may be performed at each of three or more continuous observation distances D in the observation distance range $D(1) \leq D \leq D(a)$, thereby obtaining correction coefficients.

In this embodiment, the reference image $G_1$ and the fluoroscopic image $G_2$ are normalized by the exposure times and $S_4$ of the image acquisition devices 17 and 18; however, instead of this, gains of the image acquisition devices 17 and 18 may be controlled based on the signal intensities of the reference image $G_1$ and the fluoroscopic image $G_2$, and the reference image $G_1$ and the fluoroscopic image $G_2$ may be divided by gain multiplication factors corresponding to the gains, thereby acquiring the normalized reference image $G_1'$ and the normalized fluoroscopic image $G_2'$.

Figure 12:
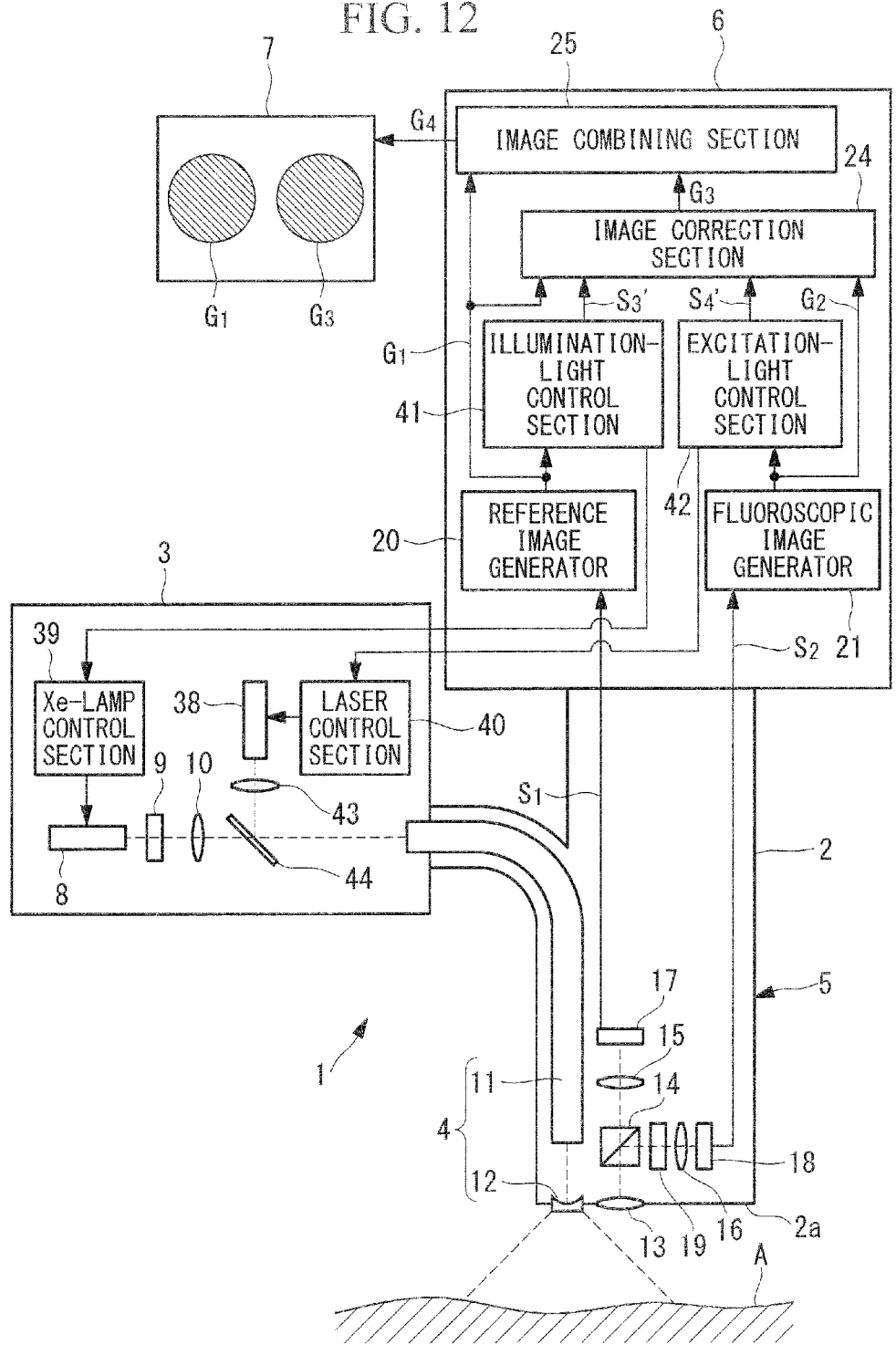
FIG. 12 is a diagram showing the entire configuration of a modification of the fluoroscopy apparatus shown in FIG. 1.

As shown in FIG. 12, in a case where the light source 3 includes a Xe lamp 8 and a laser light source 38, and the outputs therefrom can be controlled by a Xe-lamp control section 39 and a laser control section 40, thereby modulating light, the reference image $G_1$ and the fluoroscopic image $G_2$ may be divided by an intensity $S_3'$ of the illumination light and an intensity $S_4'$ of the excitation light that are calculated based on the signal intensities of the reference image $G_1$ and the fluoroscopic image $G_2$ by an illumination-light control section (ILC section) 41 and an excitation-light control section (ELC section) 42, thereby acquiring the normalized reference image $G_1'$ and the normalized fluoroscopic image $G_2'$. Reference numeral 43 denotes a focusing lens, and reference numeral 44 denotes a dichroic mirror.

Before the reference image $G_1$ and the fluoroscopic image $G_2$ are normalized, noise components of the image acquisition devices 17 and 18 may be subtracted. Thus, an advantage is afforded in that calculation precision can be improved.

An example case where white light is used as illumination light, and near-infrared fluorescence is used as fluorescence has been described above; however, the present invention is not limited thereto. The present invention can be applied to any fluorochrome such as one for which excitation light in the visible region serves as reference light and fluorescence in the visible region serves as fluorescence.

Since fluorescence and reflected light have different dependences of acquired brightness on observation distance, there is a problem in that the influence of distance is not sufficiently corrected by just dividing a fluoroscopic image by a reflected-light image.

However, with regard to the fluoroscopy apparatus 1 and the fluoroscopy method according to the embodiment of the present invention, an advantage is afforded in that observation can be performed by using a highly-quantitative fluoroscopic image obtained after any distance dependence remaining in a divided image is sufficiently eliminated.

REFERENCE SIGNS LIST

A observation target (subject)
1 fluoroscopy apparatus
2 insert member
3 light source
4 illumination unit (illumination section)
6 image correction section
17 image acquisition device (return-light image acquisition section)
18 image acquisition device (fluoroscopic image acquisition section)
28 correction-coefficient setting section (correction coefficient storage)
33 longitudinal motion stage (distance control section)

The invention claimed is:

1. A fluoroscopy apparatus comprising:
an illumination section that includes a light source for radiating illumination light and excitation light onto a subject;
a fluoroscopic image acquisition section that acquires a fluoroscopic image of fluorescence generated in the subject irradiated with the excitation light from the illumination section;
a return-light image acquisition section that acquires a reference image of return light returning from the subject irradiated with the illumination light from the illumination section;
a distance-information acquisition section that acquires information about a distance between the return-light image acquisition section and the subject; and
an image correction section that corrects the fluoroscopic image acquired by the fluoroscopic image acquisition section, by using the reference image acquired by the return-light image acquisition section,
wherein the image correction section is configured to calculate correction coefficients obtained by power approximation applied to the distance-information of the signal intensity of the fluoroscopic image and the reference image, the image correction section also configured to generate at least one of a correction reference image and a correction fluoroscopic image, the correction reference image generated through a power calculation applied to light intensity information of the reference image using the correction coefficient of the reference image, the correction fluoroscopic image generated through a power calculation applied to light intensity information of the fluoroscopic image using the correction coefficient of the fluoroscopic image,
the image correction further configured to divide the fluoroscopic image by the correction reference image, divide the correction fluoroscopic image by the reference image or divide the correction fluoroscopic image by the correction reference image.

2. The fluoroscopy apparatus according to claim 1, wherein the distance-information acquisition section acquires the distance information from a signal intensity of the reference image acquired by the return-light image acquisition section.

3. The fluoroscopy apparatus according to claim 2,
wherein the image correction section comprises a correction coefficient storage that stores the distance information in association with the correction coefficient; and
the correction coefficient stored in the correction coefficient storage is read by using the distance information acquired by the distance-information acquisition section.

4. The fluoroscopy apparatus according to claim 3,
wherein the correction coefficient storage is configured to set a predetermined observation distance as a boundary value by using the distance information that is acquired by the distance-information acquisition section and stores the correction coefficients that are different before and after the boundary value.

5. The fluoroscopy apparatus according to claim 1, further comprising a distance control section that moves the subject toward or away from the return-light image acquisition section,
wherein the distance-information acquisition section is a displacement sensor provided in the distance control section.

6. The fluoroscopy apparatus according to claim 5,
wherein the image correction section comprises a correction coefficient storage that stores the distance information in association with the correction coefficient; and
the correction coefficient stored in the correction coefficient storage is read by using the distance information acquired by the distance-information acquisition section.

7. The fluoroscopy apparatus according to claim 6,
wherein the correction coefficient storage is configured to set a predetermined observation distance as a boundary value by using the distance information that is acquired by the distance-information acquisition section and stores the correction coefficients that are different before and after the boundary value.

8. The fluoroscopy apparatus according to claim 1,
wherein the image correction section comprises a correction coefficient storage that stores the distance information in association with the correction coefficient; and
the correction coefficient stored in the correction coefficient storage is read by using the distance information acquired by the distance-information acquisition section.

9. The fluoroscopy apparatus according to claim 8,
wherein the correction coefficient storage is configured to set a predetermined observation distance as a boundary value by using the distance information that is acquired by the distance-information acquisition section and stores the correction coefficients that are different before and after the boundary value.

10. A fluoroscopy method comprising:
radiating, from an illumination section, illumination light and excitation light onto a subject;
acquiring a fluoroscopic image of fluorescence generated in the subject irradiated with the excitation light from the illumination section;
acquiring, with a return-light image acquisition section, a reference image of return light returning from the subject irradiated with the illumination light from the illumination section;
acquiring information about a distance between the return-light image acquisition section and the subject;
correcting the fluoroscopic image by the reference image;
calculating correction coefficients obtained by power approximation applied to the distance-information of the signal intensity of the fluoroscopic image and the reference image;
generating at least one of a correction reference image and a correction fluoroscopic image, the correction reference image generated through a power calculation applied to light intensity information of the reference image using the correction coefficient of the reference image, the correction fluoroscopic image generated through a power calculation applied to light intensity information of the fluoroscopic image using the correction coefficient of the fluoroscopic image; and
dividing the fluoroscopic image by the correction reference image, dividing the correction fluoroscopic image by the reference image or dividing the correction fluoroscopic image by the correction reference image.

* * * * *